United States Patent [19]

Hershberger et al.

[11] Patent Number: 4,753,886

[45] Date of Patent: Jun. 28, 1988

[54] PLASMID PHJL210 AND RELATED BIFUNCTIONAL CLONING VECTORS FOR USE IN STREPTOMYCETES

[75] Inventors: Charles L. Hershberger, New Palestine; Jeffrey L. Larson, Indianapolis, both of Ind.

[73] Assignee: Eli Lilly and Company, Indianapolis, Ind.

[21] Appl. No.: 639,566

[22] Filed: Aug. 10, 1984

[51] Int. Cl.$^4$ .................... C12N 1/20; C12N 15/00; C12N 1/00; C12R 1/465

[52] U.S. Cl. ................... 435/253; 435/172.3; 435/243; 435/320; 435/886; 435/889; 435/896; 536/27; 935/6; 935/29; 935/75

[58] Field of Search ............... 435/68, 70, 91, 172.3, 435/253, 317, 886, 889, 896, 243, 172.1, 317.1, 320; 536/27; 935/6, 29, 75

[56] References Cited

U.S. PATENT DOCUMENTS 4,416,994  11/1983  Nakatsukasa et al. .............. 435/253

FOREIGN PATENT DOCUMENTS 8202901  2/1982  PCT Int'l Appl. ............. 435/172.3
1557774  12/1979  United Kingdom .

OTHER PUBLICATIONS

Bibb et al., 1977, *J. Mol. Gen. Genet.* 154:155.
Bibb and Hopwood, 1978, *Microbiology* 1978:139.
Bibb et al., 1980, *Developments in Industrial Microbiology* 21:55.
Bibb et al., 1980, *Nature* 284:526.
Schottel et al., 1981, *J. of Bactriology* 146(1):360.
Manis and Highlander, 1982, *Gene* 18:13.
Ogura et al., 1980, Proc. Natl. Acad. Sci. 77:3993.
Larson and Hershberger, 1984, *J. of Bacteriology* 157(1):314.
Bibb, et al., 1985, Mol. Gen. Genet., 199:26-36.
Thompson et al., 1982, Gene 20:51-62.
Larson and Hershberger, 1986, *Plasmid* 15:199-209.

*Primary Examiner*—James Martinell
*Attorney, Agent, or Firm*—Gerald V. Dahling; Leroy Whitaker

[57] ABSTRACT

The present invention discloses selectable, recombinant DNA shuttle vectors for use in streptomycetes and *E. coli*. The shuttle vectors of the present invention are present at moderately high copy number. The invention further discloses transformants of the aforementioned vectors.

33 Claims, 6 Drawing Sheets

Restriction Site Map of Plasmid pJL192.

pJL192

Restriction Site and Functional Map of Plasmids pHJL2200 and pHJL2201 pHJL2200 pHJL2201

Restriction Site and Functional Map of Plasmids pHJL2202 and pHJL2203 pHJL2202 pHJL2203

Restriction Site and Functional Map of Plasmid pHJL201 pHJL201

Restriction Site and Functional Map
of Plasmids pHJL200, pHJL202, pHJL203,
pHJL204 and pHJL205

Restriction Site and Functional Map of Plasmids pHJL210 and pHJL211 pHJL210 pHJL211

PLASMID PHJL210 AND RELATED BIFUNCTIONAL CLONING VECTORS FOR USE IN STREPTOMYCETES

SUMMARY OF THE INVENTION

The present invention comprises selectable, novel, moderately high copy number recombinant DNA cloning vectors comprising an ~2.5 kb KpnI origin of replication-containing restriction fragment of plasmid pJL192 and one or more DNA segments that convey resistance to at least one antibiotic when transformed into a sensitive restrictionless host cell. The vectors contain a mutant streptomycetes replicon which increases the copy number of plasmids containing the mutant replicon relative to plasmids containing the wildtype replicon present in pJL192. The invention further comprises transformants containing the aforementioned vectors.

The present invention provides selectable and moderately high copy number plasmids of about 50 copies per cell for use in streptomycetes and related host cells. Heretofore, the development and exploitation of recombinant DNA technology in streptomycetes has been retarded and made especially difficult because of the general lack of moderately high copy number vectors. Previously, very high copy number vectors of several hundred copies per cell and low copy number vectors of 1–5 copies per cell were available. The existance of moderately high copy number plasmids provides a means by which the product yield of proteins encoded by genes carried on these moderately high copy number plasmids may be increased when compared to the level of expression from genes carried on low copy number plasmids. Thus, moderately high copy number plasmids are advantageous in obtaining expression of poorly transcribed or translated genes cloned into streptomycetes without the problems of lethal expression that may occur with very high copy number plasmids. The vectors of the present invention exist in moderately high copy numbers and are functional and selectable in both streptomycetes and other host strains and therefore represent a significant advance in the technical art.

The vectors are particularly useful because they are relatively small, versatile, and can transform and be selected in any streptomycetes cell that is sensitive to an antibiotic for which resistance is conveyed and wherein the mutant replicon provides sufficient information for self-replication. Since more than seventy percent of naturally occurring antibiotics are produced by streptomycetes strains, it is desirable to develop cloning systems and vectors that are applicable to that industrially important group. The present invention provides such vectors and thus allows for the cloning of genes into streptomycetes both for increasing the yields of known antibiotics as well as for the production of new antibiotics and antibiotic derivatives.

The present invention provides vehicles for cloning DNA into streptomycetes host cells and also allows for the convenient selection of transformants. Since transformation is a very low frequency event, such a functional test is a practical necessity for determining which cell(s), of among the billions of cells, has acquired the plasmid DNA. This is important because DNA sequences that are themselves non-selectable can be inserted into the vectors and, upon transformation, cells containing the vector and the particular DNA sequence of interest can be isolated by appropriate phenotypic selection.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a change in the recipient cell.

Transformant—a recipient host cell that has undergone transformation.

Sensitive Host Cell—a host cell that cannot grow in the presence of a given antibiotic without a DNA segment that confers resistance thereto.

Restriction Fragment—any linear DNA generated by the action of one or more restriction enzymes.

Insertional Isomer—one of the two or more possible recombinant DNA molecules formed when a DNA fragment is inserted at one of two or more compatible sites on the recipient DNA or when a DNA fragment is inserted in one of the two reciprocal orientations that are possible at a site on the recipient DNA.

Replicon—a DNA sequency that controls and allows for replication of DNA.

E. coli Origin of Replication (replicon)—a DNA sequence that controls and allows for replication of a plasmid or other vector in E. coli.

Streptomycetes Origin of Replication (replicon)—a DNA sequence that controls and allows for replication of a plasmid or other vector in streptomycetes.

$Ap^R$—the ampicillin resistant phenotype.
$Tc^S$—the tetracycline sensitive phenotype.
$Nm^R$—the neomycin resistant phenotype.
$Ts^R$—the thiostrepton resistance phenotype.
kb—kilobases or 1000 nucleotide pairs

DETAILED DESCRIPTION OF THE INVENTION

The present invention comprises moderately high copy number recombinant DNA cloning vectors comprising:

(a) an ~2.5 kb KpnI origin of replication-containing restriction fragment of plasmid pJL192, and (b) one or more DNA segments that convey resistance to at least one antibiotic when transformed into a sensitive restrictionless host cell.

The invention further comprises transformants of the aforementioned vectors.

Vectors of the present invention are constructed by ligating one or more antibiotic resistance-conferring DNA segments to the ~2.5 kb KpnI origin of replication-containing restriction fragment of plasmid pJL192. The resultant vectors are then ligated to a functional origin of replication-containing and antibiotic resistance-conferring restriction fragment of an E. coli plasmid to produce self-replicating bifunctional vectors that are selectable in both E. coli and streptomycetes.

Plasmid pJL192 can be conventionally isolated from E. coli K12 C600R$_k$-M$_k$-/pJL192, a strain deposited and made part of the Northern Regional Research Laboratory, Peoria, Ill. 61604. The strain is available to the public, as a preferred source and stock reservoir of the plasmid, under the accession number NRRL B-15040. A restriction site map of plasmid pJL192 is presented in FIG. 1 of the accompanying drawings. For purposes of the present application, FIG. 1 and all subsequent figures are not drawn to scale.

Although many different streptomycetes origin of replication-containing fragments of plasmid pJL192 can be constructed, the fragments exemplified herein for illustrative purposes are characterized by the fact that all contain the ~2.5 kb KpnI restriction fragment. This ~2.5 kb KpnI restriction fragment was generated during complete KpnI enzymatic digestion of plasmid pJL192 and was found to produce moderately high copy number (forty to fifty copies per cell) derivative plasmids. Plasmid pJL192 contains an ~5.9 kb EcoRI-SalI replicon fragment from the streptomycete plasmid SCP2*, a plasmid known to have a low copy number of one to five copies per cell. It is believed that the regulatory sequence controlling the SCP2* copy number was substantially mutated upon the paring down of the SCP2* origin of replication-containing ~5.9 kb EcoRI-SalI fragment to the ~2.5 kb KpnI restriction fragment of the present application.

A desirable cloning vector for streptomycetes should contain plasmid replication functions that are expressed in streptomycetes and two markers for antibiotic resistance, preferably with a unique recognition site for a restriction enzyme in each resistance marker. In order to construct an ideal cloning vector, the ~2.5 kb KpnI origin of replication-containing restriction fragment of plasmid pJL192 can be independently ligated to one or more antibiotic resistance-conferring DNA fragments, exemplified herein for illustrative purposes by the thiostrepton resistance-conferring ~1.6 kb BamHI restriction fragment of plasmid pLR2 and the neomycin resistance-conferring ~3.4 kb BamHI restriction fragment of plasmid pLR4, to form vectors illustrative of the present invention. Plasmids pLR2 and pLR4, respective sources of the thiostrepton and neomycin resistance-conferring fragments, are constructed in accordance with and are the subject of U.S. Pat. No. 4,416,994. Both plasmids pLR2 and pLR4 are functional in E. coli and therefore can be amplified and isolated conveniently for subsequent manipulation.

For convenience and ease of construction, the thiostrepton resistance-conferring ~1.6 kb BamHI fragment and the neomycin resistance-conferring ~3.4 BamHI fragment are ligated to the ~2.5 KpnI kb origin of replication-containing fragment of plasmid pJL192 to produce plasmids illustrative of the present invention. Desirable recombinant plasmids of two orientations may result depending upon the orientation of the inserted DNA fragment. Thus, insertion of the ~1.6 kb BamHI fragment of plasmid pLR2 to the ~2.5 kb KpnI restriction fragment of plasmid pJL192 results in illustrative plasmids pHJL2200 and pHJL2201; similarly, insertion of the ~3.4 kb BamHI fragment into pHJL2200 results in illustrative plasmids pHJL2202 and pHJL2203.

Although the thiostrepton and neomycin antibiotic resistance-conferring DNA segments exemplified herein are respectively the ~1.6 kb BamHI and ~3.4 kb BamHI restriction fragments of plasmids pLR2 and pLR4, those skilled in the art can construct and use, either individually or in combination, additional DNA segments that also confer resistance to thiostrepton and neomycin. Additional thiostrepton resistance-conferring DNA segments of pLR2 include, for example, the ~13 kb PstI restriction fragment and also the ~1 kb BclI restriction fragment. Additional neomycin resistance-conferring DNA segments of plasmid pLR4 include, for example, the ~3.5 Pst restriction fragment and also the larger of the SacII-KpnI fragments of the ~3.4 kb BamHI restriction fragment. Still other DNA segments conferring resistance to the same or to different antibiotics such as, for example, chloramphenicol, hygromycin, viomycin, tylosin, erythromycin, and the like can also be constructed and used. In addition, various functional derivatives of the above described antibiotic resistance-conferring DNA segments can be constructed by adding, eliminating, or substituting certain nucleotides. Ligation of these derivatives or other antibiotic resistance-conferring DNA segments to the ~2.5 kb KpnI restriction fragment, in place of the antibiotic resistance-conferring DNA segments exemplified herein, results in plasmids that are within the scope of the present invention.

The present streptomycetes-functional vectors such as, for example, plasmids pHJL2200 and pHJL2202 can be ligated to a functional origin of replication-containing and antibiotic resistance-conferring restriction fragment of a variety of E. coli plasmids such as, for example, plasmids pBR322, pBR325, pBR328 and the like, to produce self-replicating bifunctional vectors that are selectable in both E. coli and streptomycetes. These bifunctional constructions comprise the ~2.5 kb KpnI origin of replication-containing fragment of plasmid pJL192, one or more DNA segments that confer antibiotic resistance in streptomycetes, a replicon that is functional in E. coli and also a DNA segment that confers antibiotic resistance in E. coli. The present invention discloses plasmid pHJL201, a small bifunctional plasmid of approximately 9.9 kb that contains very little extraneous sequence that does not contribute to its utility as a cloning vector. Plasmid pHJL201 is a desirable cloning vector given its relatively small size, functional construction and the presence of two BamHI restriction sites one of which is available for insertion of an additional antibiotic resistance marker or heterologous DNA. One skilled in the art will appreciate that plasmid pHJL201 can be easily generated by a KpnI digestion of plasmid pJL192.

In addition, bifunctional constructions, exemplified herein by plasmids pHJL201, pHJL210 and pHJL211 are particularly advantageous because amplification and manipulation of plasmids can be done faster and more conveniently in E. coli than in streptomycetes. Thus, after desired recombinant DNA procedures are accomplished within the E. coli host system, the plasmids can be transformed into a streptomycete host cell. Alternatively, the particular streptomycete DNA can be removed, re-constructed to plasmid form (if necessary), and then transformed into a streptomycete or a related host cell. Since the present vectors are fully selectable in streptomycetes, identification of recombinant clones can be done efficiently.

The various replicon restriction fragments of plasmids pJL192, pBR322, pBR325 and the like, and also the various antibiotic resistance-conferring DNA segments can be modified to facilitate ligation. For exampe, molecular linkers can be provided to the ~2.5 kb KpnI replicon fragment, as well as to the particular resistance-conferring DNA segments, to generate specific sites for subsequent ligation. In addition, the origin of replication-containing restriction fragments can also be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose.

The recombinant DNA cloning vectors of the present invention are not limited for use in a single species or strain of streptomycetes. To the contrary, the vectors are broadly applicable and can be transformed into host cells of many streptomycetes taxa, particularly restrictionless strains of economically important taxa that produce antibiotics such as aminoglycoside, macrolide, β-lactam, polyether, and glycopeptide antibiotic and the like. Such restrictionless strains are readily selected and isolated from streptomycetes taxa by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of streptomycetes taxa that produce aminoglycoside antibiotics and in which the present vectors are especially useful and can be transformed, include restrictionless cells of, for example: *Streptomyces kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of streptomycetes taxa that produce macrolide antibiotics and in which the present vectors are especially useful and can be transformed, include restrictionless cells of, for example: *Streptomyces caelestis* (antibiotic M188), *S. platensis* (platenomycin), *S rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus*(albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin) D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of streptomycetes taxa that produce β-lactam antibiotics and in which the present vectors are especially useful and can be transformed, include restrictionless cells of, for example: *Streptomyces lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis*, S. fimbriatus, *S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of streptomycetes taxa that produce polyether antibiotics and in which the present vectors are especially useful and can be transformed, include restrictionless cells of, for example: *Streptomyces albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

In addition to the representative streptomycetes host cells described above, the present vectors are also useful and can transform *E. coli.* Thus, vectors of the present invention have wide application and are useful and can transform host cells of a variety of organisms.

While all the embodiments of the present invention are useful, some of the present recombinant DNA cloning vectors and transformants are preferred. Accordingly, preferred vectors are plasmids pHJL2200, pHJL2202, pHJL201, pHJL210 and pHJL211; and preferred transformants are *Streptomyces griseofuscus*/pHJL2200, *S. griseofuscus*/pHJL2202, *S. lividans*/pHJL201, *S. lividans/* pHJL210, *S. lividans*/pHJL211, *S. griseofuscus*/pHJL201, *S. griseofus-* cus/pHJL210, S. griseofuscus/pHJL211, S. fradiae/pHJL201, S. fradiae/pHJL210, S. fradiae/pHJL211, E. coli K12 C600R$_k$-M$_k$-/pHJL201, E. coli K12 C600R$_k$-M$_k$-/pHJL210, and E. of this preferred group, plasmids pHJL201, pHJL210 and pHJL211 and transformants S. griseofuscus/pHJ201, S. griseofuscus/pHJL210, S. griseofuscus/pHJL211, E. coli K12 C600R$_k$-M$_k$-/pHJL201, E. coli K12 C600R$_k$-M$_k$-/pHJL210 and E. coli K12 C600R$_k$-M$_k$- /pHJL211 are most preferred.

The vectors of the present invention comprise origins of replication that are functional in E. coli and streptomycetes and therefore provide flexibility in the choice of hosts. Consequently, cloned DNA sequences can be shuttled into E. coli for construction of new plasmids, physical analysis, and for mapping of restriction sites and then shuttled back into streptomycetes for functional analysis and improvement of strains. This is particularly advantageous because amplification and manipulation of plasmids can be done faster and more conveniently in E. coli than in streptomycetes. For the present vectors can be amplified conventionally in E. coli K12 by growth with spectinomycin or chloramphenicol. This is not possible in the streptomycetes host system. In addition, since all the plasmid vectors contain resistance markers that are expressed in E. coli K12, recombinants are easily selected. Therefore, large amounts of plasmid DNA can be isolated conveniently and in a shorter time than that required for doing similar procedures in streptomycetes.

The recombinant DNA cloning vectors and transformants of the present invention have broad utility and help fill the need for suitable cloning vehicles for use in streptomycetes and related organisms. Moreover, the ability of the present vectors to confer resistance to antibiotics also provides a functional means for selecting transformants. This is important because of the practical necessity for determining and selecting the particular cells that have acquired vector DNA. Additional DNA segments, that lack functional tests for their presence, can also be inserted into the present vectors and then transformants containing the non-selectable DNA can be isolated by appropriate antibiotic selection. Such non-selectable DNA segments can be inserted at any site, except within regions necessary for plasmid function, maintainance, and replication, and include, but are not limited to, genes that specify antibiotic modification enzymes, antibiotic resistance, antibiotic biosynthesis, and regulatory genes of all types.

More particularly, a non-selectable DNA segment that comprises a gene can be inserted in a plasmid such as, for example, illustrative plasmid pHJL210, at the unique BamHI restriction site. Such an insertion inactivates the neomycin resistance gene and thus allows for the easy identification of streptomycetes transformants containing the recombinant plasmid. This is done by first selecting for thiostrepton resistance and then identifying those thiostrepton resistant transformants that are not resistant to neomycin. In a similar manner, insertion of a DNA segment of interest at, for example, the unique ClaI restriction site inactivates the thiostrepton resistance gene. Thus, transformants carring this recombinant plasmid are also identified easily by first selecting for neomycin resistance and then identifying those neomycin resistant transformants that are not resistant to thiostrepton. Therefore, the ability to select for antibiotic resistance in streptomycetes and related cells allows for efficient isolation of the extremely rare cells that contain the particular non-selectable DNA of interest.

The functional test for antibiotic resistance as described herein above, is also used to locate DNA segments that act as control or biosynthetic elements and direct expression of antibiotic resistance genes. Such segments, including but not limited to, promoters, attenuators, repressors, inducers, ribosomal binding sites, and the like, are used to control the expression of other genes in cells of streptomycetes and related organisms.

The antibiotic resistance-conferring vectors of the present invention are also useful for insuring that linked DNA segments are stably maintained in host cells over many generations. These genes or DNA fragments, covalently linked to an antibiotic resistance-conferring fragment and propagated either in streptomycetes or in E. coli, are maintained by exposing the transformants to levels of antibiotic that are toxic to non-transformed cels. Therefore, transformants that lose the vector, and consequently any covalently linked DNA, cannot grow and are eliminated from the culture. Thus, the vectors of the present invention can stabilize and maintain any DNA sequence of interest unless the cloned DNA or an expressed product is lethal to the host cell.

The cloning vectors and transformants of the present invention provide for the cloning of genes to improve yields of various products that are currently produced in streptomycetes and related cells. Examples of such products include, but are not limited to, streptomycin, tylosin, cephalosporins, actaplanin, avoparcin, narasin, monensin, apramycin, tobramycin, erythromycin, tetracycline, chloramphenicol, vancomycin, teichomycin, and the like. The present invention also provides selectable vectors that are useful for cloning, characterizing, and reconstructing DNA sequences that code for commercially important proteins such as, for example, human insuin, human proinsulin, glucagon, interferon, human growth hormone, avian growth hormone, bovine growth hormone, porcine growth hormone, interleukin I, interleukin II, and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, streptomycin, cephalosporins, tylosin, actaplanin, avoparcin, narasin, monensin, apramycin, tobramycin, tetracycline, chloramphenicol, erythromycin, teichomycin, and vancomycin derivatives, or for enzymes that mediate and increase bioproduction of antibiotics or other products.

The capability of inserting, stabilizing, and shuttling the aforementioned DNA segments into streptomycetes and E. coli allows for easy recombinant genetic manipulation for increasing the yield and availability of antibiotics that are produced by streptomycetes. In addition, since the ~2.5 kb KpnI origin of replication-containing fragment of plasmid pJL192 moderately a high copy number plasmid, almost any DNA sequence that is poorly transcribed or translated, can be readily cloned into the present vectors and shuttled between streptomycetes and E. coli.

Escherichia coli K12 C600R$_k$-M$_k$-/pJL192 (NRRL B-15040) can be cultured in a number of ways using any of several different media. Carbohydrate sources which are preferred in a culture medium include, for example, glucose and glycerol, and nitrogen sources include, for example, ammonium salts, amino acid mixtures, and peptones. Nutrient inorganic salts are also incorporated and include the customary salts capable of yielding magnesium, sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

E. coli K12 C600$R_k$-$M_k$-/pJL192 can be grown under aerobic culture conditions over a relatively wide pH range of about 6.5 to 7.5 at temperatures ranging from about 25° to 42° C. For the production of plasmid pJL192 in the greatest quantity, however, it is desirable to start with a culture medium at a pH of about 7.2 and maintain a culture temperature of about 37° C. Culturing the E. coli cells under the aforementioned conditions, results in a reservoir of cells from which the plasmid pJL192 is isolated by techniques well known in the art.

Figure 1:
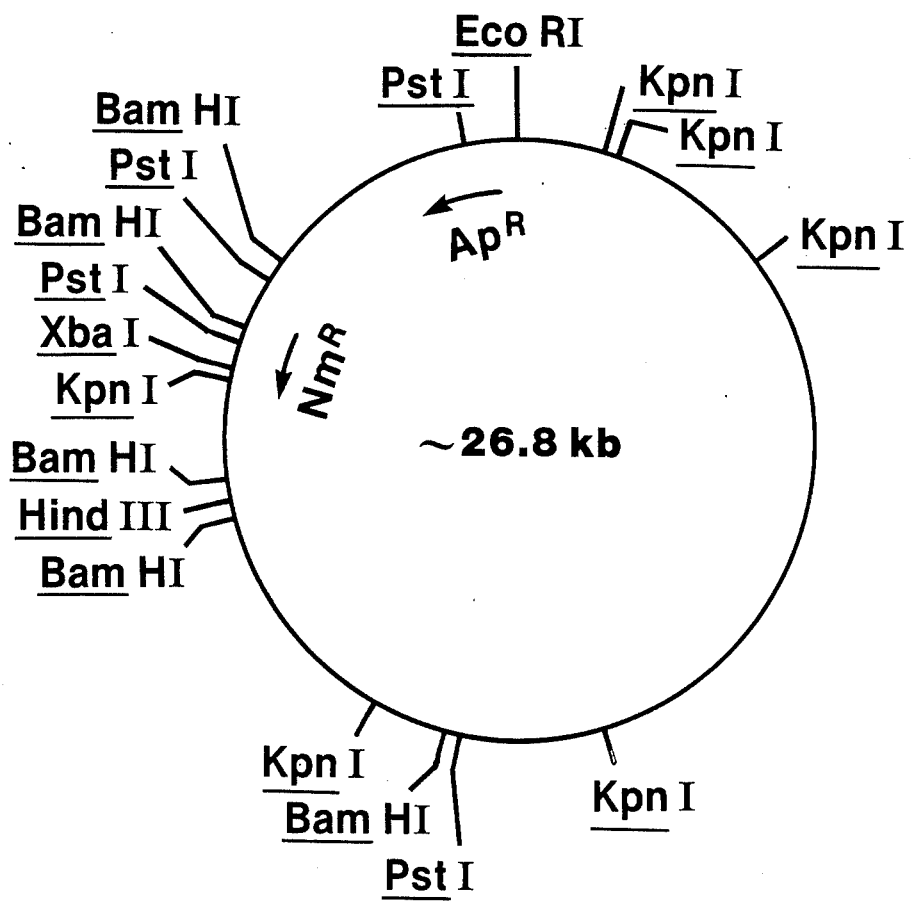
FIG. 1 shows the restriction site map of plasmid pJL192.

The following examples further illustrate and detail the invention disclosed herein. Both an explanation of and the actual procedures for constructing the invention are described where appropriate.

EXAMPLE 1

Culture of E. coli K12 C600$R_k$-$M_k$-/pJL192 and Isolation of Plasmid pJL192

A single bacterial colony of E. coli K12 C600$R_k$-$M_k$-/pJL192 (NRRL B-15040) was inoculated into LB medium which contains, per liter aqueous solution, 10 g. Bacto tryptone, 5 g. Bacto yeast extract and 10 g. NaCl (pH 7.5) with 25 μg./ml. of ampicillin according to conventional microbiological procedures. The culture was incubated at 37° C. overnight. The following morning, 500 ml. of M9 medium (Miller et al., 1979, Experiments in Molecular Genetics, Cold Spring Harbor Laboratories, Cold Spring Harbor, N.Y.) supplemented with 1 mM MgSO$_4$, 0.2% glucose, 0.3–4% CAA (casamino acids, Difco), 2 μg./ml. B1 (thiamine-HCl, Sigma) and additives were inoculated with 5 ml. of the overnight culture. The culture was incubated with vigorous shaking at 37° C. overnight and the next morning samples of the overnight culture were inoculated at dilutions of 1/10 to 1/50 into the supplemented M9 media and incubated with vigorous shaking at 37° C. for 2½ to 3 hours. The turbidity of the culture measured with the blue filter was approximately 300 to 400 Klett units. Chloramphenicol (150–175 μg./ml.) was added to the culture and incubation with vigorous shaking was continued overnight.

The bacterial cells were harvested by centrifugation at 7500 rpm for 5 minutes at 4° C. and then washed twice with 200 ml. of SV (0.15M NaCl, 0.1M NaEDTA pH 8.0). The pellet was resuspended in 10 ml./gm. wet weight TS solution (25% sucrose, 50 mM Tris, pH 8) and placed on ice. To this suspension, 2 ml./gm. wet weight of lysozyme (5 mg./ml. in 50 mM Tris-HCl pH 7.8) was added and left to chill on ice for 5 minutes. Next, 4 ml./gm. wet weight of 0.25M EDTA pH 8.0 was added and chilled for another 5 minutes. Upon the addition of 16 ml./gm. wet weight lysis solution ( 0.4% deoxycholate, 1% Brij 58, 50 mM Tris and 0.0625M EDTA, pH 8) the mixture was incubated at 37° C. for 15–30 minutes. The DNA was recovered by centrifugation in a Sorvall SS34 rotor at 21,000 rpm for 15–30 minutes at 4° C. The supernatant was saved and 0.1 vol. of 3M NaOAc, at pH 8 and 0.64 volumes isopropanol were added to the supernatant. The DNA was centrifuged at 10,000 rpm for 10 minutes at 4° C., whereupon the pellet was resuspended in 0.1 volume TE (10 mM Tris, 1 mM EDTA pH 8). The plasmid DNA was purified by centrifugation to equilibrium in cesium chloride density gradients containing propidium diiodide according to known techniques.

EXAMPLE 2

Construction of Streptomycetes-Functional Plasmids pHJL2200, pHJL2201, pHJL2202 and pHJL2203

A. KpnI Digestion of Plasmid pJL192 and Isolation of the ~2.5 kb Origin of Replication-Containing Restriction Fragment About 20 μl. (20 μg.) of plasmid pJL192 DNA, 5 μl. BSA (Bovine Serum albumin, 1 mg./ml.), 19 μl. water, 1 μl. of KpnI (8 units/μl) restriction enzyme*, and 5 μl. reaction mix** were incubated at 37° C. for 2 hours and then terminated by heating at 70° C. for 10 minutes. The DNA was precipitated with 0.1 volume 3M NaOAc pH 8, followed by two volumes 100% ethanol. The precipitation can be done either at −20° C. overnight or at −70° C. (on dry ice) for at least 15 minutes. The DNA precipitate was washed once with cold 70% ethanol and then dried and resuspended in 50 μl. TE (10 mM Tris, 1 mM EDTA pH 8.0). The resulting DNA was electrophoresed on horizontal agarose gels in 1X TBE buffer (89 mM Tris-HCl pH 8.3, 89 mM Boric acid, 2.5 mM EDTA) in substantial accordance with the teaching of Maniatis et al., 1982, Molecular Cloning, Cold Spring Harbor Laboratories, Cold Spring Harbor, N.Y.
*Restriction enzymes and instructions can be obtained from the following sources:
New England Bio Labs., Inc. 32 Tozer Road Beverly, Mass. 01915
Boehringer-Männheim Biochemicals 7941 Castleway Drive P.O. Box 50816 Indianapolis, Ind. 46250
Bethesda Research Laboratories Inc. 8717 Grovemont Circle P.O. Box 577 Gaithersburg, Md. 20760
**Reaction mix for KpnI restriction enzyme was prepared with the following composition.
60 mM NaCl
60 mM Tris. HCl, pH 7.5
60 mM MgCl$_2$
60 mM 2-mercaptoethanol The separated fragments were located in the gel by staining with ethidium bromide and visualizing fluorescent bands with ultraviolet light. A slice adjacent to the desired ~2.5 kb band was made and DEAE-cellulose (Whatman DE-81) paper was placed in the slit. The DNA was electrophoresed until the DNA was completely bound to the paper. Upon removal, the paper was washed once in 100 mM KCl and 10 mM Tris-HCl, pH 8 and dispersed in 5 ml. of elution buffer (1M NaCl and 10 mM Tris-HCl, pH 8) by vigorous shaking. The paper was removed by filtration through siliconized pyrex wool and the DNA was either directly precipitated with 2 volumes ethanol or diluted by addition of 1 volume water, followed by ethanol precipitation. Either method of precipitation can be performed on dry ice for an hour or, alternatively, overnight at −20° C. Following precipitation, the fragment was redissolved in 100–500 μl. TE buffer for subsequent ligation.

B. Digestion and Isolation of the Thiostrepton Resistance-Conferring Fragment of Plasmid pLR2

About 20 μg. of plasmid pLR2 DNA, the construction of which is disclosed in U.S. Pat. No. 4,416,994 and incorporated herein by reference, is digested with the restriction enzyme BamHI* which cleaves the plasmid at four sites. The BamHI-generated ends are filled in with Klenow Polymerase I as described in Maniatis et al., 1982. These blunt-end fragments are next combined with KpnI linkers (consisting of a self complementary oligonucleotide of the sequence:pCGGTACCG available from Collaborative Research, Inc., 128 Spring Street, Lexington, Mass. 02173), providing a KpnI ceavage site for ligation to the ~2.5 kb KpnI origin of replication-containing fragment of plasmid pJL192. The 20 μg. of DNA fragments obtained from pLR2 are treated with 10 units T4 DNA ligase** in the presence of 200 picomoles of the 5'-phosphorylated synthetic oligonucleotide pCGGTACCG and in 20 μl. T4 DNA ligase buffer (20 mM Tris, pH 7.6, 0.5 mM ATP, 10 mM MgCl$_2$, 5 mM dithiothreitol) at 20°-22° C. overnight. The solution is then heated 10 minutes at 70° C. to halt ligation. The linkers are cleaved by KpnI digestion and the fragments, now with KpnI ends, are separated usinq 1 percent AGE (agarose gel electrophoresis). The ~1.6 kb fragment is isolated from the gel by first staining with ethidium bromide and then locating the fragment with ultraviolet light and eluting on paper as described in Example 2A above.

*Reaction mix for BamHI restriction enzyme was prepared with the following composition.
1.5M NaCl
60 mM Tris-HCl, pH 7.9
60 mM MgCl$_2$

**T4 DNA ligase can be obtained from the following sources:
New England Bio Labs., Inc. 32 Tozer Road Beverly, Mass. 01915
Bethesda Research Laboratories P.O. Box 577 Gaithersburg, Md. 20760
Boehringer-Mannheim Biochemicals 7941 Castleway Drive P.O. Box 50816 Indianapolis, Ind. 46250

C. Ligation to Form Plasmids pHJL2200 and pHJL2201

Figure 2:
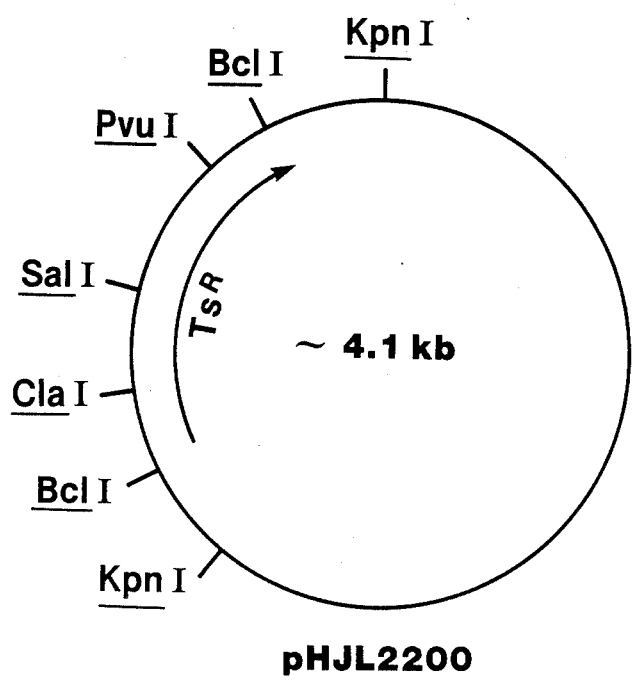
FIG. 2 is a restriction site and functional map of plasmids pHJL2200 and pHJL2201.
Figure 2:
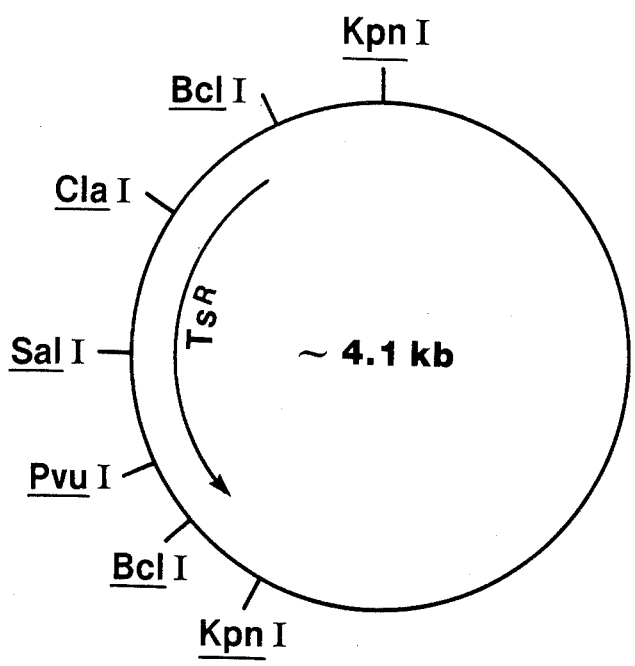

About 20 μl. of the ~2.5 kb KpnI fragment of plasmid pJL192 DNA (Example 2A), 20 μl. of the ~1.6 kb BamHI fragment with konI linkers of plasmid pLR2 DNA (Example 2B), 10 μl. - of 5x kinase/ligase buffer (Example 4B), and 1 μl. of T4 DNA ligase are incubated at 16° C. for 4 hours. The ligation may then be used directly in the transformation of streptomycetes. A restriction site and functional map of plasmids pHJL2200 and pHJL2201 is presented in FIG. 2 of the accompanying drawings.

D. Partial BclI Digestion of Plasmid pHJL2200

The desired digestion is carried out in substantial accordance with the teaching of Example 2A except that plasmid pHJL2200, BclI restriction enzyme and reaction mix* are used in place of plasmid pJL192 and KpnI restriction enzyme and reaction mix. Additionally, the reaction is carried out at 50° C. and terminated by two phenol extractions, three ether extractions, an ethanol precipitation and then resuspended in water for subsequent AGE treatment.

*Reaction mix for BclI restriction enzyme was prepared with the following composition.
750 mM KCl
60 mM Tris-HCl, pH 7.4 at 25° C.
100 mM MgCl$_2$
10 mM Dithiothreitol

E. Digestion and Isolation of the ~3.4 kb BamHI Fragment of Plasmid pLR4

The desired digestion is carried out in substantial accordance with the teaching of Example 2A except that plasmid pLR4, the construction of which is disclosed in U.S. Pat. No. 4,416,994 and incorporated herein by reference, and BamHI restriction enzyme are used in place of plasmid pJL192 and KpnI restriction enzyme.

F. Ligation to Form Plasmids pHJL2202 and pHJL2203

Figure 3:
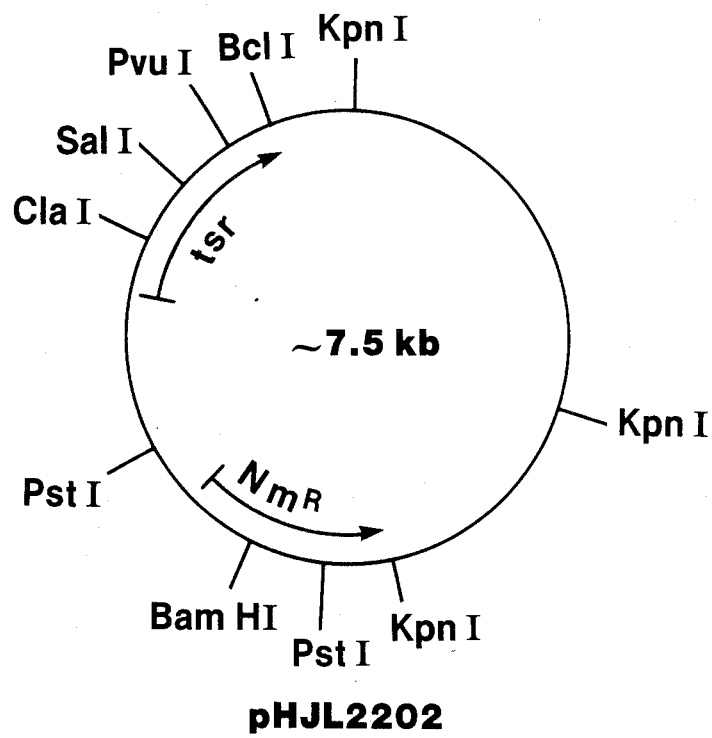
FIG. 3 is a restriction site and functional map of plasmids pHJL2202 and pHJL2203.
Figure 3:
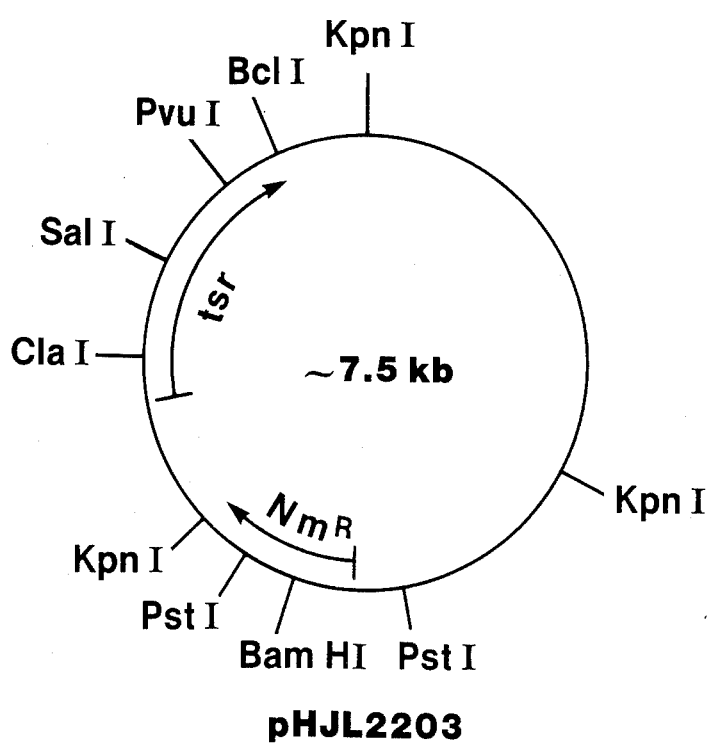

The desired ligation is carried out in substantial accordance with the teaching of Example 2C. Recombinant plasmids of four orientations with the desired phenotype can be produced because the ~3.4 kb BelI neomycin resistance-conferring fragment can be oriented in either direction at one of two BamHI sites in plasmid pHJL2200. A restriction site and functional map of plasmids pHJL2202 and pHJL2203 is presented in FIG. 3 of the accompanying drawings.

EXAMPLE 3

Construction of *Streptomyces griseofuscus*/pHJL2200 and *S. griseofuscus*/pHJL2202

A. Growth of Cultures for Preparation of Protoplasts

A vegetative inoculum was conventionally prepared by growing *S. griseofuscus*, a strain deposited and made part of the permanent stock culture collection of the American Type Culture Collection, Rockville, Md. 20852, from which it is available to the public under the accession number ATCC 23916, under submerged conditions for 20 hours at 30° C. in TSB* supplemented with 0.4% glycine. The procedure for protoplasting *S. griseofuscus* is time-consuming and is generally performed as follows. Streak out *S. griseofuscus* on a plate containing YMX agar (0.3% yeast extract, 0.3% malt extract, 0.2% dextrose and 2% agar. Approximately 48 hours later, inoculate a single bacterial colony into 10 ml. TSB*; homogenize and incubate at 30° C. overnight. Next, homogenize 4 ml. of the overnight culture and add 100 ml. TSB supplemented with 0.4% glycine and incubate overnight at 30° C. Repeat this procedure the following afternoon using fresh overnight culture. The folowing morning, add 50 ml. of 50% (v/v) glycerol to the culture and freeze 15 ml. samples at −20° C. The frozen cells can be stored for six months and used for transformation. Thaw the frozen cells by placing the tube at room temperature in a beaker of water. Harvest the cells in a bench top centrifuge and wash three times in 10 ml. of 10.3% sucrose. Resuspend the cell pellet in 10 ml. of P medium (Hopwood and Wright, 1978, J. Molecular and General Genetics 162:307) supplemented with lysozyme (1 mg./ml.) and incubate at 30° C. for 2 hours. Centrifuge to pellet the protoplasts and wash the pellet three times in 10 ml. P medium, vortexing and pipetting the pellet into solution at each wash. Resuspend the final pellet in 2 ml. P medium for subsequent transformation.

*Trypticase soy broth is obtained from Difco Laboratories, Detroit, Mich. or Baltimore Biological Laboratories, P.O. Box 243, Cockeysville, Md. 21031.

B. Transformation

About 10 μl. of plasmid DNA in ligation buffer and about 150 μl. of *S. griseofuscus* protoplasts are mixed slightly in a test tube. To this mixture add about 101 μl. 50% PEG 1000 (polyethylene glcol, Sigma) in P medium and pipet to mix. After a 1-2 minute wait, add P medium to bring the volume up to 1 ml. Plate the transformed cells on R2 medium and incubate overnight at 30° C. Overlay the regenerating protoplasts with 3 ml. R2 overlays containing 400 μg./ml. thiostrepton and incubate at 30° C. for at least 4 days. The resulting *S. griseofuscus*/pHJL2200 thiostrepton resistant colonies can be isolated according to known procedures, cultured, and then conventionally identified in accordance with the teaching of Example 3C. The transformant culture can then be used for subsequent production and isolation of plasmid DNA.

*S. griseofuscus*/pHJL2202 transformants can be selected for thiostrepton resistance and neomycin resistance by overlaying the regenerating protoplasts with R2 overlay supplemented with neomycin at 50 μg./ml. and thiostrepton at 400 μg./ml. The resultinq *S. griseofuscus*/pHJL2202 thiostrepton and neomycin resistant colonies are isolated according to known procedures and then identified in accordance with the teaching of Example 3C.

C. Analysis of *S. griseofuscus* Transformants

The resultant transformants are cultured on YMX agar (0.3% yeast extract, 0.3% malt extract, 0.2% dextrose and 2% agar) supplemented with thiostrepton (40 μg./ml.) to obtain single colonies. These colonies are used to inoculate 10 ml. TSB cultures containing thiostrepton (40 μg./ml.). The cultures are homogenized and grown overnight at 30° C. in a rotary shaker.

The culture is homogenized and added to 200 ml. TSB and 0.4% glycine supplemented with thiostrepton (40 μg./μl.) and grown one to two days at 30° C. The cells are harvested in a Sorvall GSA rotor at 10,000 rpm for 15 minutes. The cells are resuspended in 100 ml. TE containing 25% sucrose and lysozyme (5 mg./ml.). After incubation at 37° C. for one hour, 50 ml. of 0.25M NaEDTA, pH 8.0 is added. 25 ml. samples are transferred to Sorvall tubes containing 1 ml. 20% w/v SDS (sodium dodecyl sulfate) and mixed gently at room temperature for 20-30 minutes to lyse the cells. After 8 ml. of 5M NaCl are added and mixed gently at room temperature for 30 minutes, the cells are put on ice for 1½ hours. The DNA is recovered by centrifugation in a Sorvall rotor at 15,000 rpm for 20 minutes. The supernatant is collected and the DNA precipitated with 0.64 vol. isopropanol and centrifuged for 20 minutes at 10,000 rpm. The supernatant is decanted and the DNA pellet is air dried and then resuspended in 10 ml. TE buffer where it can then be purified by CsCl equilibrium gradients as taught in Example 1.

EXAMPLE 4

Construction of Plasmids pHJL200, pHJL201, pHJL202, pHJL203, pHJL204, and pHJL205

A. Partial KpnI Digestion of Plasmid pJL192

The following digestion was set up. About 13 μl. plasmid pJL192 DNA (about 3.25 μg.) prepared according to the teaching of Example 1, 25 μl. water, 5 μl. BSA, 5 μl. 10x KpnI restriction buffer and 2 μl. KpnI enzyme were mixed and incubated at 37° C. At 15, 30, 60, 90, and 120 minute intervals, 10 μl. aliquots were removed, mixed with 40 μl. water and heated at 70° C. for 10 minutes. This protocol produces all possible reaction products ranging from molecules that have not been cleaved by the KpnI restriction enzyme to those that have been completely digested by the KpnI restriction enzyme. These aliquots were precipitated with 1/10 volume 3M NaOAc, pH 8 and 2 volumes ethanol and frozen at −70° C. for 1 hour.

B. Ligation

Figure 4:
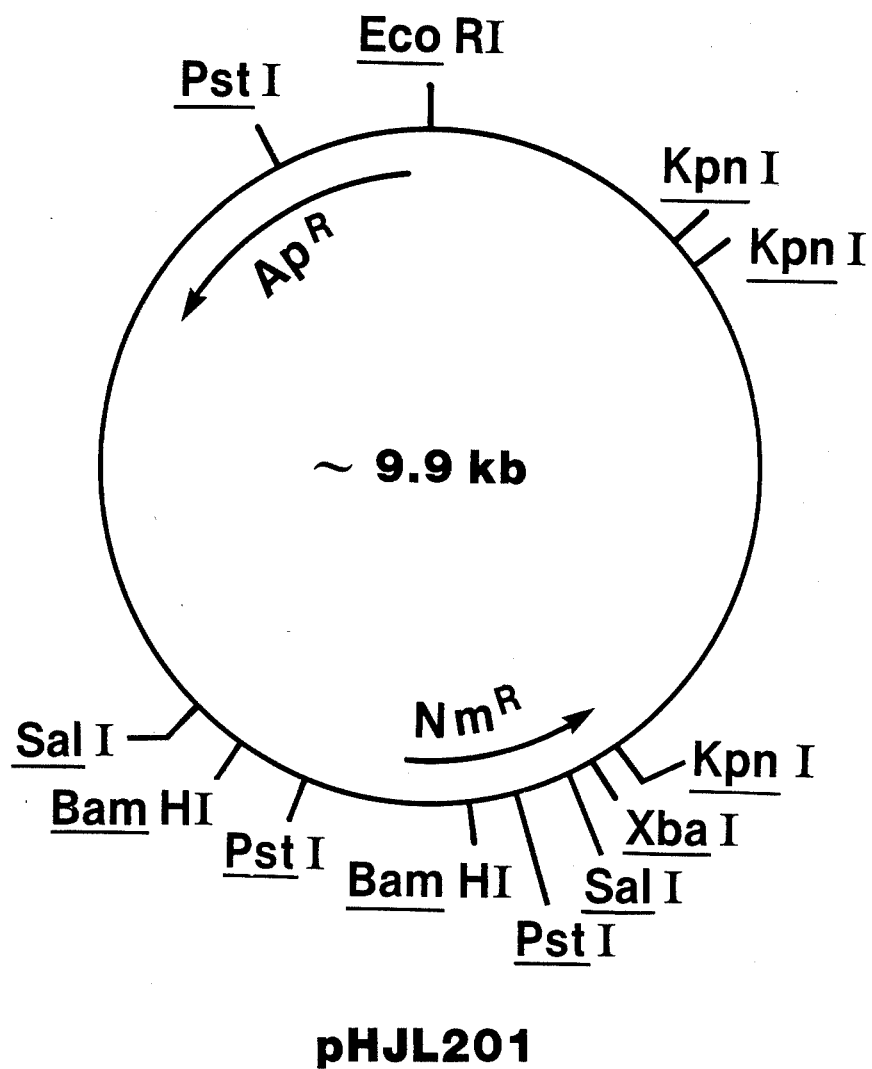
FIG. 4 is a restriction site and functional map of plasmid pHJL201.
Figure 5:
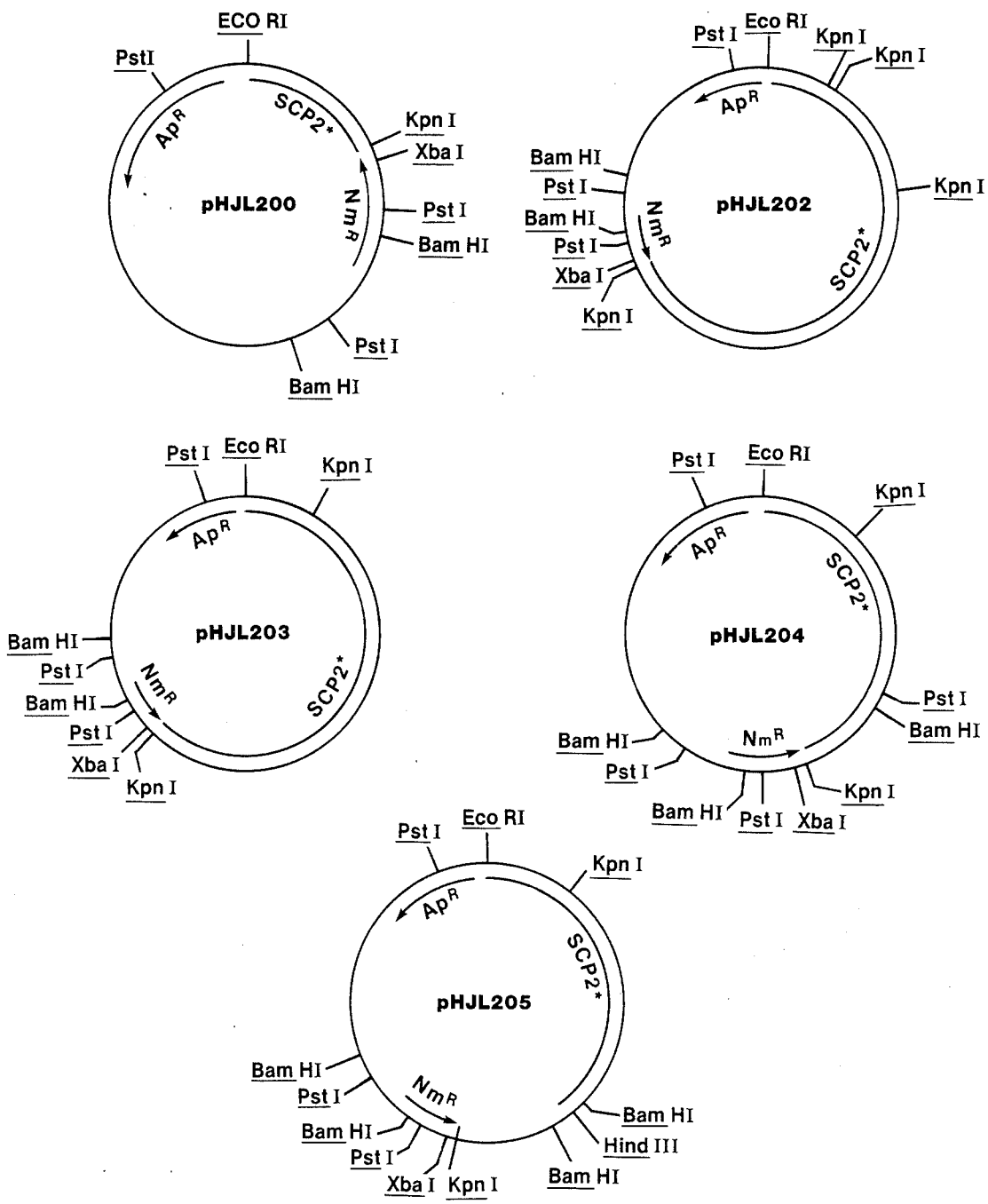
FIG. 5 is a restriction site and functional map of plasmids pHJL200, pHJL202, pHJL203, pHJL204 and pHJL205.
Figure 6:
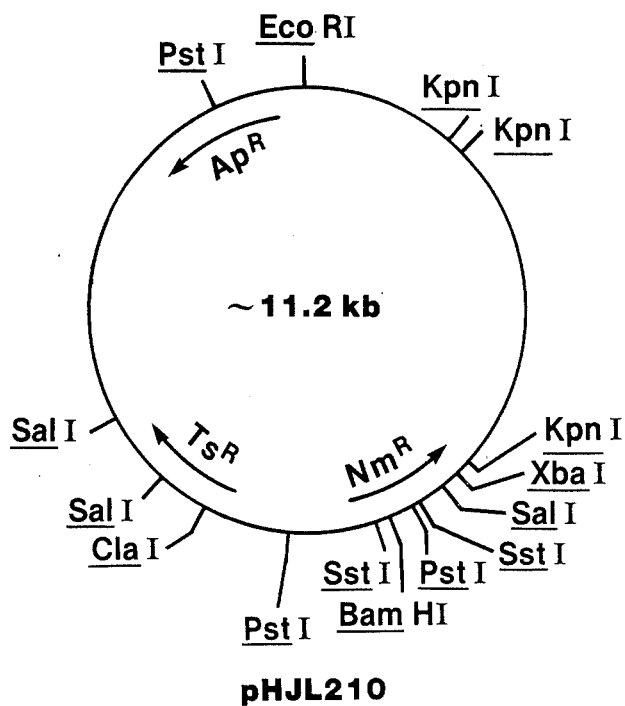
FIG. 6 is a restriction site and functional map of plasmids pHJL210 and pHJL211.
Figure 6:
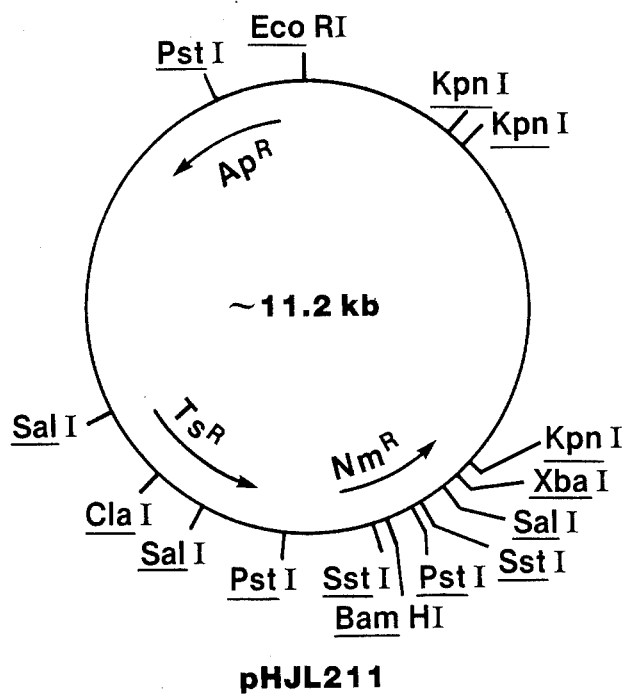

The precipitates were collected, washed twice, air dried and then resuspended in 20 μl. water. 6 μl. of each reaction was removed and mixed with a solution of 20 μl. 5x kinase/ligase buffer*, 40 μl. 0.66M ATP, pH 7.4, 33 μl. water and 1 μl. T4 DNA ligase (Boehringer Mannheim ~1 unit/μl.) and incubated at 15° C. for 72 hours to promote self-circularization. After incubation, 50 μl. was removed from each reaction and the reactions were terminated by increasing the temperature to 70° C. for 10 minutes. These reactions were precipitated as above and resuspended in 15 μl. water. A restriction site and functional map of plasmid pHJL201 is presented in FIG. 4 of the accompanying drawings. FIG. 5 illustrates a restriction site and functional map of plasmids pHJL200, pHJL202, pHJL203, pHJL204 and pHJL205.

*5x kinase/ligase buffer was prepared with the following composition.
250 mM Tris-HCl, pH7.8
25% Glycerol
25 mM Dithiothreitol
50 mM MgCl₂

EXAMPLE 5

Construction of *E. coli* K12 C600R$_k$-M$_k$-/pHJL201, *E. coli* K12 C600R$_k$-M$_k$-/pHJL200, *E. coli* K12 C600R$_k$-M$_k$-/pHJL202, *E. coli* K12 C600R$_k$-M$_k$-/pHJL203, *E. coli* K12 C600R$_k$-M$_k$-/pJHL204, and *E. coli* K12 C600R$_k$-M-/pHJL205

A. Preparation of Frozen Competent *E. coli* K12 C600R$_k$-M$_k$-

Fresh overnight cultures of *E. coli* K12 C600R$_k$-M$_k$-, a strain widely available and on deposit with the ATCC under the accession number ATCC 33525, were subcultured 1:10 in fresh L-broth (disclosed in Miller, 1972, Experiments in Molecular Genetics, Cold Spring Harbor Labs, Cold Spring Harbor, N.Y.) and grown at 37° C. for 1 hour. A total of 660 Klett Units of cells were harvested, washed with 2.5 ml. of 100 mM NaCl₂, suspended in 2.5 ml. of 150 mM CaCl₂ and incubated at room temperature for 20 minutes. The cells were harvested by centrifugation, resuspended in 0.5 ml. of 150 mM CaCl₂-10% glycerol, chilled on ice for 3-5 minutes and frozen. The suspensions of cells were stored in liquid nitrogen until use. Preservation and storage did not adversely affect the viability or frequency of transformation by covalently closed circular DNA.

B. Transformation

The competent cells were thawed in an ice bath and mixed in a ratio of 0.1 ml. of cells to 0.05 ml. of DNA (12.5 μl. of the sample disclosed in Examples 4B and 6C and 37.5 μl. of 0.1XSSC (0.015M NaCl, 0.0015M Sodium Citrate at pH 7). The transformation mixture was chilled on ice for 20 minutes, heat shocked at 42° C. for 1 minute and chilled on ice for 10 minutes. The samples were then diluted with 0.85 ml. of L-broth, incubated at 37° C. for 1.5 hours, spread on L-agar containing ampicillin (50 µg./ml.) and incubated for 18 hours at 37° C. The resulting colonies of correct phenotype (Ap$^R$, Tc$^S$) were screened for plasmid size in substantial accordance with the method of in-the-wall-lysis as described by Eckhardt et al., 1978, Plasmid 1:584. These resulting colonies constituted the desired E. coli K12 C600R$_k$-M$_k$-/pHJL201, E. coli K12 C600R$_c$C600R$_k$-M$_k$-/pHJL202, E. coli K12 C600R$_k$-M$_k$-/pHJL203, E. coli K12 C600R$_k$-M$_k$/pHJL204 and E. coli K12 C600R$_k$-M$_k$-/pHJL205 transformants. The ampicillin resistant and tetracycline sensitive colonies were isolated according to known procedures, cultured, and used to purify covalently closed circular DNA which was then conventionally identified by restriction enzyme and AGE analysis of the constitutive plasmids. The identified transformants were then used for subsequent production and isolation of plasmids pHJL201, pHJL200, pHJL202, pHJL203, pHJL204, and pHJL205 according to the teaching of Example 1 except that strains containing the desired plasmid were used instead of E. coli K12 C600R$_k$-M$_k$-/pJL192.

EXAMPLE 6

Construction of Plasmids pHJL210 and pHJL211

A. Partial BamHI Digestion of Plasmid pHJL201

About 10 µl. (10 µg.) of plasmid pHJL201 (prepared according to the teaching of Example 5), 5 µl. BSA (1 mg./ml.), 29 µl. water, 1 µl. of BamHI (diluted 1:4 with water) restriction enzyme, and 5 µl. BamHI reaction mix were incubated at 37° C. for 15 minutes. The reaction was terminated by heating to 70° C. for 10 minutes. The partial digestion products corresponding to full length linear molecules of the plasmid were purified away from the smaller complete digestion products by AGE according to the teaching of Example 1. The DNA was precipitated in substantial accordance with the teaching of Example 4. The resulting DNA precipitate was resuspended in 20 µl. water for subsequent ligation.

B. Isolation of the ~1 kb BclI Restriction Fragment of Plasmid pLR2

Most E. coli K12 strains methylate certain residues in their DNA. For example, a methylase specified by the dam gene methylates at the N6 position of the indicated adenine in the DNA sequence 5'GA$^{me}$TC3'. This methylation has been shown to interfere with cleavage of DNA by some (but not all) restriction endonucleases whose recognition sequences comprise or include the methylated sequences. BclI, a restriction enzyme commonly used in this invention, will not cleave the BclI recognition sequence 5'TGATCA3' if it has been methylated. To avoid this problem, plasmid pLR2 should be transferred to an E. coli dam$^-$ strain such as GM48, a strain deposited and made part of the permanent stock culture collection of the Northern Regional Research Laboratory, Peoria, Ill. The strain is available to the public under the accession number NRRL B-15725.

The desired digestion is subsequently carried out in substantial accordance with the teaching of 2B except that BclI restriction enzyme is used in place of BamHI restriction enzyme. The ~1 kb BclI restriction fragment was purified by AGE according to the teaching of Example 1.

C. Ligation

The desired ligation was carried out in substantial accordance with the teaching of Example 2C. Plasmids of various construction may be formed but the desired recombinant plasmids were those that phenotypically will confer resistance to neomycin and thiostrepton. Additionally, recombinant plasmids of two orientations were produced because the ~1 kb BclI resistance-conferring fragment can be oriented in either direction. A restriction site and functional map of plasmids pHJL210 and pHJL211 is presented in FIG. 5 of the accompanying drawings.

EXAMPLE 7

Construction of E. coli K12 C600R$_k$-M$_k$-/pHJL210 and E. coli K12 C600R$_k$-M$_k$-/pHJL211

The desired constructions were individually made, selected, and recovered in substantial accordance with the teaching of Example 5, with the exception that plasmids pHJL210 and pHJL211 were used in place of plasmids pHJL200, pHJL201, pHJL202, pHJL203, pHJL204 and pHJL205.

EXAMPLE 8

Construction of Streptomyces griseofuscus/pHJL201 S. griseofuscus/pHJL210 and S. griseofuscus/pHJL211

The desired constructions were individually made, selected, and recovered in substantial accordance with the teaching of Example 3, with the exception that plasmid pHJL201, rather than plasmid pHJL2200 was used and in the selection, top agar containing sufficient neomycin to give a final plate concentration of 2 µg./µl. was used in place of thiostrepton. Similarly, the construction of pHJL210 and pHJL211 were individually made, selected, and recovered in substantial accordance with the teaching of Example 3 except that plasmids pHJL210 and pHJL211 were used in place of pHJL2202.

EXAMPLE 9

Construction of Streptomyces lividans/pHJL201, S. lividans/pHJL210 and S. lividans/pHJL211

The desired constructions were individually made, selected, and recovered in substantial accordance with the teaching of Example 8 except that Streptomyces lividans, rather than S. griseofuscus, was used. S. lividans is an old and well-known strain which is available to the public under the accession number NRRL B-15826 which is on deposit and made part of the Northern Regional Research Laboratory, Peoria, Ill. 61604. In addition, the media for protoplasting and growing S. lividans and the preparation of protoplasts and transformation are as described in International Patent Publication (of International Patent Application No. PCT/BG79/00095) No. WO79/01169, Example 2. The identified transformants were then used for subsequent production and isolation of plasmids pHJL201, pHJL210 and pHJL211 according to known procedures essentially as taught in Example 3C.

EXAMPLE 10

Construction of Streptomyces fradiae/pHJL201, S. fradiae/pHJL210, and S. fradiae/pHJL211

The desired constructions were individually made, selected, and recovered in substantial accordance with the teaching of Example 8 except that *streptomycetes fradiae*, rather than *S. griseofuscus*, was used. *S. fradiae* is an old and well-known strain which is available to the public under the accession number ATCC 19609 which is on deposit and made part of the American Type Culture Collection, 12301 Parklawn Drive, Rockville, Md. 20852. In addition, the TSB medium for protoplasting and growing *S. fradiae* was modified and contained only 0.2% glycine. *S. fradiae* transforms at very low frequencies because of an endogenous restriction system, therefore the number of transformants per µg. of DNA is substantially less for *S. fradiae* hosts transformed with pHJL201, pHJL210, and pHJL211 than for *S. griseofuscus* or *S. lividans* hosts. However, plasmid DNA isolated from *S. fradiae* gives a high frequency of transformation when it is restransformed into *S. fradiae*.

We claim:

1. A moderately high copy number recombinant DNA cloning vector comprising:
    (a) the origin of replication-containing KpnI restriction fragment approximately 2.5 kb in size of plasmid pJL192,
    (b) one or more DNA segments that convey resistance to at least one antibiotic when transformed into a sensitive restrictionless host cell;
    (c) said vector capable of replicating to a moderately high copy number in said host cells.

2. A recombinant DNA cloning vector selected from the group consisting of plasmids pHJL200, phJL202, pHJL203, pHJL204 and pHJL205.

3. A DNA molecule consisting of the approximately 2.5 kb Kpn I fragment of pJL192.

4. The recombinant DNA cloning vector of claim 1 selected from the group consisting of plasmids pHJL2200, pHJL2201, pHJL2202 and pHJL2203.

5. The cloning vector of claim 4 which is pHJL2200.

6. A transformed restrictionless host cell comprising a recombinant DNA cloning vector of claim 1.

7. The transformed host cell of claim 6 which is a streptomycete.

8. The transformed host cell of claim 6 in which the recombinant DNA cloning vector is selected from the group consisting of plasmids pHJL2200, pHJL2201, pHJL2202 and pHJL2203.

9. The transformed host cell of claim 8 which is a restrictionless streptomycete.

10. The transformed streptomycete of claim 9 which is *Streptomyces griseofuscus*.

11. The transformed streptomycetes of claim 9 which is *Streptomyces lividans*.

12. The transformed host cell of claim 9 which is *Streptomyces griseofuscus*/pHJL2200.

13. The transformed host cell of claim 9 which is *Streptomyces lividans*/pHJL2200.

14. A recombinant DNA cloning vector of claim 1 comprising in addition:
    (d) a restriction fragment comprising an *E. coli* origin of replication.

15. The recombinant DNA cloning vector of claim 14 wherein the functional origin of replication-containing fragment of the *E. coli* plasmid is selected from the group consisting of fragments of plasmids pBR322, pBR325 and pBR328.

16. The recombinant DNA cloning vector of claim 15 which is selected from the group consisting of plasmids pHJL201, pHJL210 and pHJL211.

17. The recombinant DNA cloning vector of claim 16 which is plasmid pHJL201.

18. The recombinant DNA cloning vector of claim 16 which is plasmid pHJL210.

19. The recombinant DNA cloning vector of claim 16 which is plasmid pHJL211.

20. A transformed restrictionless host cell comprising a recombinant DNA cloning vector of claim 14.

21. The transformed host cell of claim 20 wherein the origin of replication-containing fragment in the vector is a restriction fragment of plasmid pBR322.

22. The transformed host cell of claim 20 which is *Streptomyces griseofuscus*/pHJL201.

23. The transformed host cell of claim 20 which is *Streptomyces griseofuscus*/pHJL210.

24. The transformed host cell of claim 20 which is *Streptomyces griseofuscus*/pHJL211.

25. The transformed host cell of claim 20 which is *Streptomyces lividans*/pHJL201.

26. The transformed host cell of claim 20 which is *Streptomyces lividans*/pHJL210.

27. The transformed host cell of claim 20 which is *Streptomyces lividans*/pHJL211.

28. The transformed host cell of claim 20 which is *E. coli* C600R$_k$-M$_k$-/pHJL201.

29. The transformed host cell of claim 20 which is *E. coli* C600R$_k$-M$_k$-/pHJL210.

30. The transformed host cell of claim 20 which is *E. coli* C600R$_k$-M$_k$-/pHJL211.

31. The transformed host cell of claim 20 which is *Streptomyces fradiae*/pHJL201.

32. The transformed host cell of claim 20 which is *Streptomyces fradiae*/pHJL210.

33. The transformed host cell of claim 20 which is *Streptomyces fradiae*/pHJL211.

* * * * *